US012575754B2

(12) United States Patent
Zhang et al.

(10) Patent No.: US 12,575,754 B2
(45) Date of Patent: Mar. 17, 2026

(54) THREE-DIMENSIONAL VENTILATION IMAGE GENERATION METHOD, AND CONTROLLER AND APPARATUS

(71) Applicants: BEIJING HUARUI BOSHI MEDICAL IMAGING TECHNOLOGY CO., LTD., Beijing (CN); TSINGHUA UNIVERSITY, Beijing (CN)

(72) Inventors: Ke Zhang, Beijing (CN); Xin Zhang, Beijing (CN); Mingtao Guan, Beijing (CN); Yibing Wang, Beijing (CN)

(73) Assignees: BEIJING HUARUI BOSHI MEDICAL IMAGING TECHNOLOGY CO., LTD., Beijing (CN); TSINGHUA UNIVERSITY, Beijing (CN)

( * ) Notice: Subject to any disclaimer, the term of this patent is extended or adjusted under 35 U.S.C. 154(b) by 397 days.

(21) Appl. No.: 18/268,891

(22) PCT Filed: Nov. 24, 2021

(86) PCT No.: PCT/CN2021/132763
§ 371 (c)(1),
(2) Date: Jun. 21, 2023

(87) PCT Pub. No.: WO2022/160899
PCT Pub. Date: Aug. 4, 2022

(65) Prior Publication Data
US 2024/0057887 A1     Feb. 22, 2024

(30) Foreign Application Priority Data
Jan. 26, 2021    (CN) .......................... 202110111098.8

(51) Int. Cl.
| | |
|---|---|
| A61B 5/0536 | (2021.01) |
| A61B 5/00 | (2006.01) |
| A61B 5/085 | (2006.01) |

(52) U.S. Cl.
CPC ............ *A61B 5/0536* (2013.01); *A61B 5/085* (2013.01); *A61B 5/086* (2025.01); *A61B 5/725* (2013.01); *A61B 5/7267* (2013.01); *A61B 5/7278* (2013.01); *A61B 2576/02* (2013.01)

(58) Field of Classification Search
CPC ....... A61B 5/0536; A61B 5/085; A61B 5/086; A61B 5/725; A61B 2576/02; A61B 5/004; A61B 5/026; A61B 2562/046
See application file for complete search history.

(56) References Cited

U.S. PATENT DOCUMENTS

2019/0142299 A1*    5/2019    Holzhacker .......... A61B 5/0536
600/390

FOREIGN PATENT DOCUMENTS

| | | |
|---|---|---|
| CN | 102793551 A | 11/2012 |
| CN | 109864712 A | 6/2019 |
| CN | 110072452 A | 7/2019 |

(Continued)

OTHER PUBLICATIONS

Electrical impedance tomography in 3D using two electrode planes: characterization and evaluation, Justin Wagenaar, Physiological Measurement, vol. 37, No. 6, DOI 10.1088/0967-3334/37/6/922 (Year: 2016).*

(Continued)

*Primary Examiner* — Sean P Dougherty
(74) *Attorney, Agent, or Firm* — Procopio, Cory, Hargreaves & Savitch LLP

(57) ABSTRACT
A three-dimensional ventilation image generation method, and a controller and an apparatus. The method comprises: generating a three-dimensional ventilation image by means (Continued)

S110 — Extracting a ventilation-related signal by means of a signal extraction algorithm from an electrical impedance signal obtained by performing electrical impedance measurement on a target region to be measured S120 — Reconstructing a three-dimensional ventilation image by means of an image reconstruction algorithm and according to the ventilation-related signal of a signal extraction algorithm and an image reconstruction algorithm and according to an electrical impedance signal obtained by performing electrical impedance measurement on a target region to be measured, wherein performing electrical impedance measurement on said target region is implemented by using an electrode array that is three-dimensionally distributed on the periphery of said target region.

11 Claims, 15 Drawing Sheets

(56) References Cited

FOREIGN PATENT DOCUMENTS

| | | | |
|---|---|---|---|
| CN | 111067521 | A | 4/2020 |
| CN | 112057073 | A | 12/2020 |

OTHER PUBLICATIONS

Measurement of ventilation and cardiac related impedance changes with electrical impedance tomography, Grant, Critical Care, 5, Article No. R37 (2011) (Year: 2011).*
Dominant-Current Deep Learning Scheme for Electrical Impedance Tomography, Eir, IEEE, vol. 66, Issue 9 (Year: 2019).*
Event-triggered averaging of electrical impedance tomography (EIT) respiratory waveforms as compared to low-pass filtering for removal of cardiac related impedance changes, Coppadoro, Journal of Clinical Monitoring and Computing (2020) 34:553-558 (Year: 2019).*
International Search Report (with translation) and Written Opinion received in corresponding International Application No. PCT/CN2021/132763, mailed Feb. 10, 2022, in 12 pages.

* cited by examiner

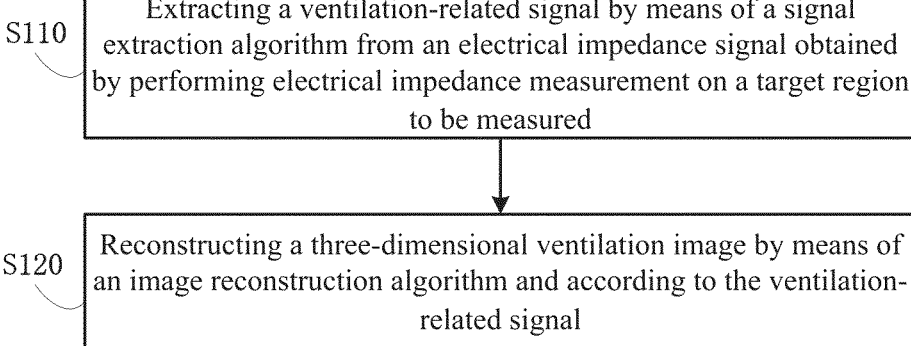

S110

Extracting a ventilation-related signal by means of a signal extraction algorithm from an electrical impedance signal obtained by performing electrical impedance measurement on a target region to be measured

S120

Reconstructing a three-dimensional ventilation image by means of an image reconstruction algorithm and according to the ventilation-related signal

FIG. 1

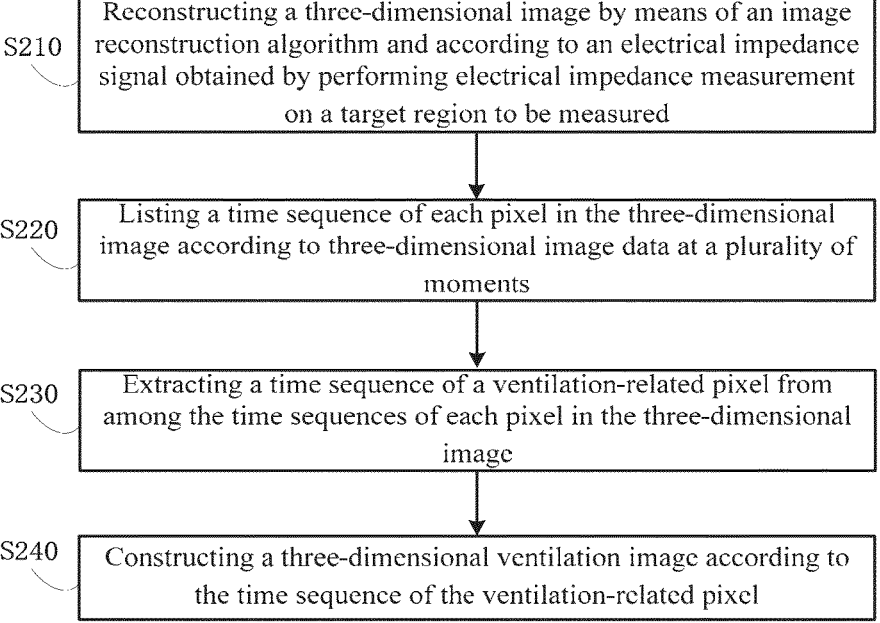

S210 — Reconstructing a three-dimensional image by means of an image reconstruction algorithm and according to an electrical impedance signal obtained by performing electrical impedance measurement on a target region to be measured S220 — Listing a time sequence of each pixel in the three-dimensional image according to three-dimensional image data at a plurality of moments S230 — Extracting a time sequence of a ventilation-related pixel from among the time sequences of each pixel in the three-dimensional image S240 — Constructing a three-dimensional ventilation image according to the time sequence of the ventilation-related pixel

FIG. 2

THREE-DIMENSIONAL VENTILATION IMAGE GENERATION METHOD, AND CONTROLLER AND APPARATUS

CROSS REFERENCE TO RELATED APPLICATIONS

This application is a 371 national stage application of International Patent Application No. PCT/CN2021/132763, filed, Nov. 24, 2021, which claims the priority of Chinese Patent Application No. CN202110111098.8 filed on Jan. 26, 2021, entitled "Three-Dimensional Ventilation Image Generation Method, and Controller and Apparatus," which is incorporated herein by reference in its entirety.

TECHNICAL FIELD

The present disclosure relates to the field of electrical impedance tomography application, and more particularly relates to a method, controller, and apparatus for three-dimensional ventilation image generation.

BACKGROUND

Electrical impedance tomography (EIT) is a non-invasive technique that aims to reconstructing image of an in vivo tissue by reflecting electrical resistivity distribution within a human body or other living body. The human body is a volume bioelectric conductor and each tissue or organ therein has a certain impedance. When a local organ of the human body has a lesion, the impedance of the corresponding local site inevitably varies relative to other sites, which allows for lesion diagnosis via impedance measurement.

Conventional techniques can only achieve a two-dimensional ventilation image that reflects change of electrical impedance induced by gas volume variation within some section of a to-be-measured thoracic region of a human body. However, the two-dimensional image can hardly reflect ventilation status of the thoracic cavity of a human body within a certain volume of a three-dimensional space.

Therefore, a method, controller, and apparatus for three-dimensional ventilation image generation are needed.

SUMMARY OF THE INVENTION

A technical problem to be solved by the disclosure is how to generate a three-dimensional ventilation image that reflects the ventilation status of a human thoracic cavity within various volumes of a three-dimensional space.

To overcome the above problems, the disclosure provides a method, controller, and apparatus for three-dimensional ventilation image generation.

In a first aspect, the present disclosure provides a three-dimensional ventilation image generation method, comprising: generating a three-dimensional ventilation image by means of a signal extraction algorithm and an image reconstruction algorithm and according to an electrical impedance signal obtained by performing electrical impedance measurement on a target region to be measured, wherein the performing electrical impedance measurement on a target region to be measured is implemented by using an electrode array three-dimensionally distributed on the periphery of the target region to be measured.

In a second aspect, the present disclosure provides a three-dimensional ventilation image generation controller, comprising a memory and a processor, wherein a computer program is stored on the memory and when being executed by the processor, implements the method described above.

In a third aspect, the present disclosure provides a three-dimensional ventilation image generation apparatus, comprising: an electrode array three-dimensionally distributed on an periphery of a target region to be measured, which is configured to perform electrical impedance measurement on the t target region to be measured and transmit a measured electrical impedance to a three-dimensional ventilation image generation controller; and the three-dimensional ventilation image generation controller described above.

Other features and advantages of the present disclosure will be explained in the description below, which partially become apparent from the description or partially become understood via implementing the disclosure. The objectives and other benefits of the disclosure may be realized and derived via specific structures illustrated in the description, claims and accompanying drawings.

BRIEF DESCRIPTION OF THE DRAWINGS

The accompanying drawings are provided for further understanding the disclosure and constitute a part of the specification, which, together with the embodiments of the present disclosure, may be used for explaining the disclosure, but do not constitute limitation to the disclosure. In the accompanying drawings:

FIG. 1 is a flow diagram of a three-dimensional ventilation image generation method according to a first embodiment of the disclosure;

FIG. 2 is another flow diagram of the three-dimensional ventilation image generation method according to the first embodiment of the disclosure;

FIG. 9(*b*) is a frequency-domain signal schematic diagram of a ventilation-related signal after the example pixel in FIG. 7 has been subjected to data filtering;

DETAILED DESCRIPTION OF THE EMBODIMENTS

Figure 3A:
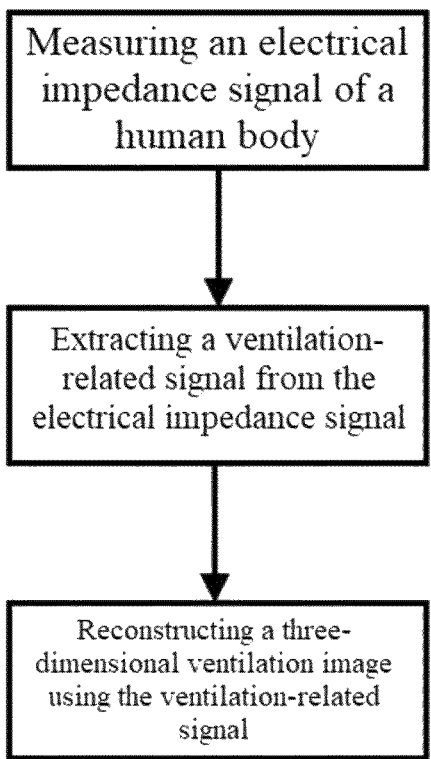
FIG. 3(a) is a flow diagram of a three-dimensional ventilation image generation method according to a second embodiment of the disclosure.

Hereinafter, the embodiments of the disclosure will be elaborated through embodiments with reference to the accompanying drawings such that how the disclosure uses technical means to solve technical problems and how the technical effects are achieved will become sufficiently understood and implementable. It is noted that without conflicts, various embodiments and respective features in the embodiments may be combined with each other, and a technical solution resulting from such combination falls within the protection scope of the disclosure.

Embodiment 1

To solve the above technical problems in the existing technologies, an embodiment of the present disclosure provides a three-dimensional ventilation image generation method, which are implementable in two manners as illustrated in FIG. 1 and FIG. 2, respectively.

Referring to FIG. 1, the three-dimensional ventilation image generation method according to this embodiment comprises steps of:

S110: a ventilation-related signal is extracted by means of a signal extraction algorithm from an electrical impedance signal obtained by performing electrical impedance measurement on a target region to be measured. Herein the operation of performing electrical impedance measurement on said target region is implemented by using an electrode array three-dimensionally distributed on the periphery of the target region to be measured, and the electrode array may be a plurality of impedance straps or an electrode vest where the electrodes are three-dimensionally distributed.

Step S120: a three-dimensional ventilation image is reconstructed by means of an image reconstruction algorithm and according to the ventilation-related signal.

In an embodiment, the electrical impedance signal comprises a ventilation-related signal and a blood-perfusion-related signal. The step of extracting a ventilation-related signal by means of a signal extraction algorithm from the electrical impedance signal obtained by performing electrical impedance measurement on the target region to be measured comprises: extracting the ventilation-related signal using a lowpass filter from the electrical impedance signal obtained by performing electrical impedance measurement on the target region to be measured, wherein the lowpass filter has a cutoff frequency greater than the second harmonic frequency of the ventilation-related signal but lower than the fundamental frequency of the blood-perfusion-related signal.

In step S110, the signal extraction algorithm refers to any one of a frequency-domain filtering algorithm, a principal component analysis algorithm, and a neural network algorithm.

In step S120, the image reconstruction algorithm refers to a linear differential reconstruction algorithm or a neural-network-based image reconstruction algorithm.

Referring to FIG. 2, the three-dimensional ventilation image generation method according to this embodiment comprises the following steps:

S210: a three-dimensional image is reconstructed by means of an image reconstruction algorithm and according to an electrical impedance signal obtained by performing electrical impedance measurement on a target region to be measured. Herein, the operation of performing electrical impedance measurement to the target region to be measured is implemented by an electrode array that is three-dimensionally distributed on the periphery of the target region to be measured.

S220: a time sequence of each pixel in the three-dimensional image is listed according to three-dimensional image data at a plurality of moments. Herein, the time sequence of each pixel is comprised of values of each pixel at the different moments.

S230: a time sequence of a ventilation-related pixel is extracted from among the time sequences of each pixel in the three-dimensional image.

S240: a three-dimensional ventilation image is constructed according to the time sequence of the ventilation-related pixel.

In step S230, the operation of extracting a time sequence of a ventilation-related pixel from among the time sequences of each pixel in the three-dimensional image is implemented by any one of the frequency-domain filtering algorithm, the principal component analysis algorithm, and the neural network algorithm.

In step S210, the image reconstruction algorithm refers to a linear differential reconstruction algorithm or a neural-network-based image reconstruction algorithm.

Embodiment 2

To solve the above technical problems in the existing technologies, embodiments of the present disclosure provide a three-dimensional ventilation image generation method applicable to a human body thoracic cavity based on the first embodiment, in which the three-dimensional ventilation image generation method in this embodiment is implemented in two manners, as illustrated in FIG. 3(*a*) and FIG. 3(*b*), respectively.

As illustrated in FIG. 3(*a*), the three-dimensional ventilation image generation method in this embodiment comprises the following steps: first, electrical impedance measurement is performed on a human body thoracic region to be measured; then, a ventilation-related signal is extracted from a measured signal; and finally, a three-dimensional ventilation image is reconstructed. Specific steps of the method are described below:

In the first step, electrical impedance measurement is performed on the human body thoracic region to be measured. In the electrical impedance measurement, first an electrode array is required to be fixed surrounding the human body thoracic cavity to be measured. The electrode array comprises a plurality of electrodes distributed in a three-dimensional space. Then, the human body thoracic cavity to be measured is excited via the electrode array and a response produced therefrom is measured, i.e., applying electrical current excitation to the electrodes alternately, and measuring voltage signals produced therefrom on the other electrodes.

Figure 4A:
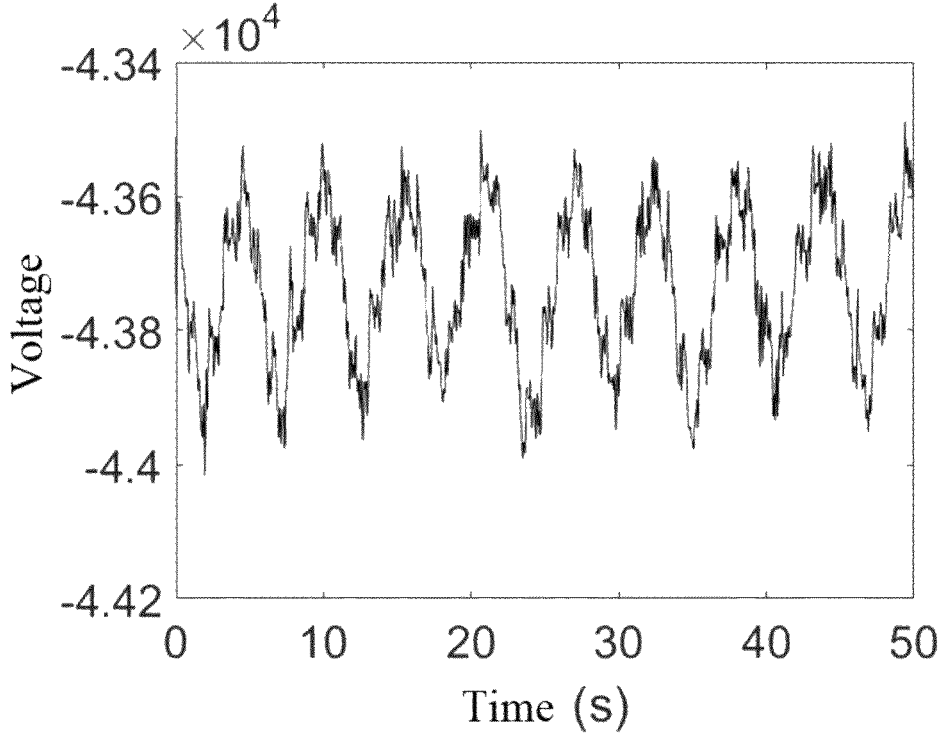
FIG. 4(a) is a temporal-domain signal schematic diagram of human body thoracic cavity measurement data according to the second embodiment of the disclosure.
Figure 4B:
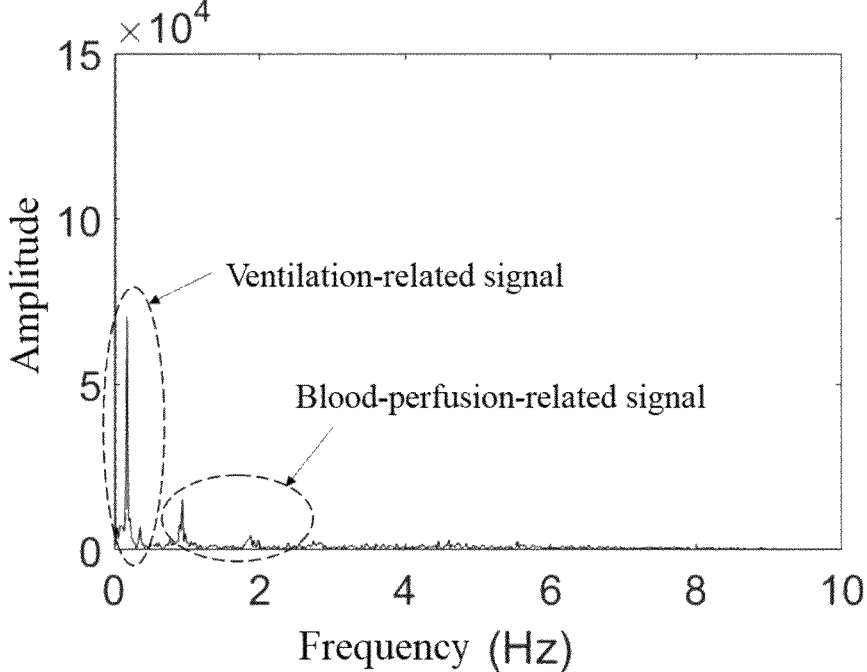
FIG. 4(b) is a frequency-domain signal schematic diagram of the human body thoracic cavity measurement data according to the second embodiment of the disclosure.
Figure 5A:
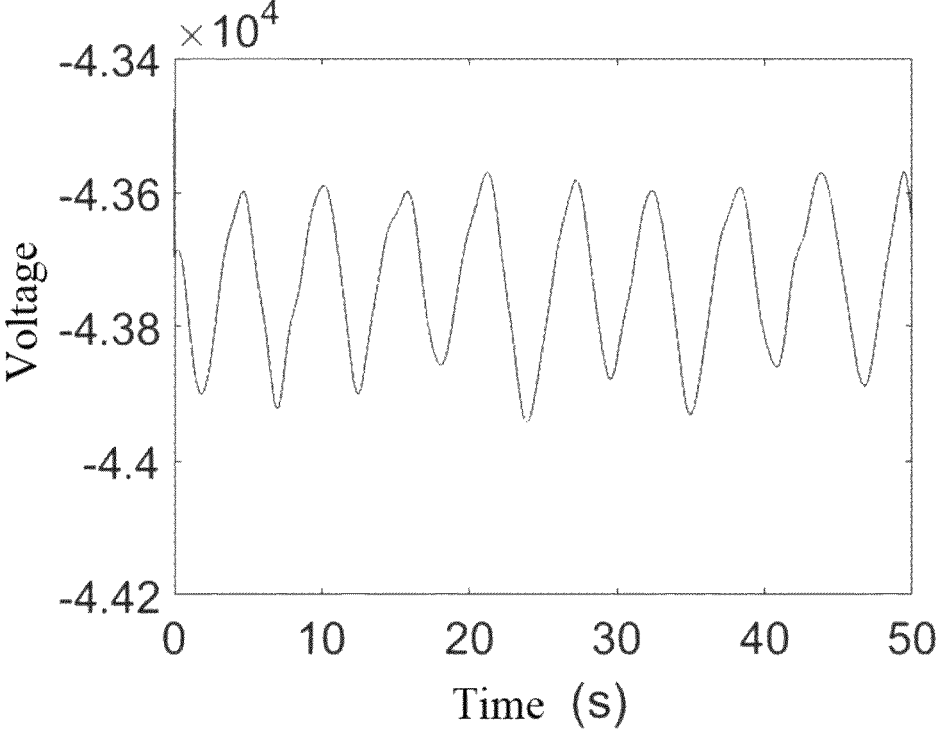
FIG. 5(a) is a temporal-domain signal schematic diagram of a ventilation-related signal after the human body thoracic cavity measurement data have been filtered according to the second embodiment of the disclosure.
Figure 5B:
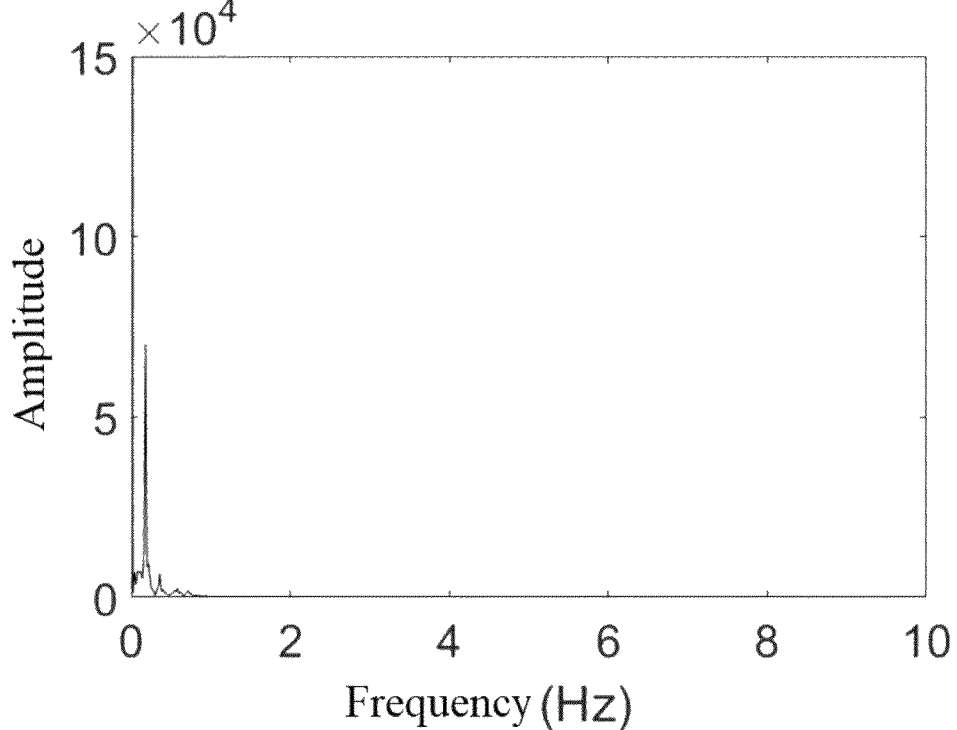
FIG. 5(b) is a frequency-domain signal schematic diagram of a ventilation-related signal after the human body thoracic cavity measurement data have been filtered according to the second embodiment of the disclosure.

In the second step, a ventilation-related signal is extracted from the electrical impedance signal obtained by the preceding step. In an embodiment of this step, the ventilation-related signal is extracted from the measured electrical impedance signal using a filter. The filter may refer to a finite pulse response filter or an infinite pulse response filter. Embodiments of measuring the human body thoracic cavity will be illustrated below. FIG. 4(a) illustrates a temporal-domain signal of the measurement data, in which the curve represents a voltage signal measured on a specific electrode during excitation. The data obtained during other excitation-measurement processes are derived in a similar manner. It is noted that in the figure, the longitudinal coordinate represents the values directly read from a digital voltage meter, which have not been converted into voltage values yet. FIG. 4(b) illustrates a frequency-domain signal of the measurement data, wherein the signal illustrated in FIG. 4(b) is derived from the signal in FIG. 4(a) via Fourier transformation. In FIG. 4(b), the ventilation-related signal and the blood-perfusion-related signal may be differentiated. To extract the ventilation-related signal, a lowpass filter, which may be a finite pulse response lowpass digital filter, may be designed with a cutoff frequency greater than the second harmonic frequency of the ventilation-related signal and lower than the fundamental frequency of the blood-perfusion-related signal. FIGS. 5(a) and 5(b) illustrate images of the filtered signal, respectively, in which FIG. 5(a) illustrates a temporal-domain signal image and FIG. 5(b) illustrates a frequency-domain signal image.

In another embodiment of this step, the ventilation-related signal is extracted using a principal component analysis (PCA) algorithm. Specifically, assuming a measurement signal is denoted as u, with a size of $N_t \times N_c$, where $N_t$ denotes the number of sample points and $N_c$ denotes the characteristic number (which refers to the number of measurement paths herein). The principal components $\{p_1, p_2, \ldots, p_{N_c}\}$ of the signal are obtained by using a principal component analysis, where the size of $p_i (i=1, 2, \ldots, N_c)$ is $N_t \times 1$ and their corresponding characteristic values decrease sequentially. By using a first and early plurality of principal components (e.g., $p_1$ and $p_2$) as a template, a template match filtering is performed on the signal u, so as to obtain a ventilation-related signal $u_V$.

In a further embodiment of this step, the ventilation-related signal is extracted using the neural-network-based algorithm. Specifically, the neural-network-based algorithm has two phases, i.e., training and predicting. In the training phase, a ventilation-related signal extraction network is trained using a supervised or non-supervised method based on training data; and in the predicting phase, the ventilation-related signal in the electrical impedance measurement signals is extracted using the well-trained ventilation-related signal extraction network.

In the third step, the three-dimensional ventilation image is reconstructed by means of an image reconstruction algorithm and according to the ventilation-related signal extracted in the second step. The three-dimensional ventilation image reflects an electrical impedance change induced by respiration in the human body region to be measured. In an embodiment of this step, the image reconstruction algorithm refers to a linear differential reconstruction algorithm. An example of reconstructing the three-dimensional ventilation image using the linear differential reconstruction algorithm will be illustrated below.

Assuming that the temporal-domain form of the ventilation-related signal extracted in the second step is u(t), where t denotes a temporal variable, the EIT differential reconstruction may be expressed as a least square problem:

$$\min_{\delta\sigma} \|J \cdot \delta\sigma - \delta u\|^2 + \alpha \|R \cdot \delta\sigma\|^2,$$

where J denotes a Jacobian Matrix, $\delta u = u(t) - u(t_{ref})$ denotes change of the signal at the moment t relative to the reference moment $t_{ref}$, $\delta\sigma$ denotes conductivity change induced by ventilation in the human body between the two moments, R denotes a regularization matrix, and a denotes a regularization parameter. The reference moment $t_{ref}$ may be set invariable during the entire image reconstruction process or may be set to dynamically update with the promotion of the image reconstruction process. $\delta\sigma$ is defined in a discrete three-dimensional mode, for example, a tetrahedral mesh or voxel mesh. Then a solution to the above problem is:

$$\delta\sigma^* = (J^T \cdot J + \alpha R^T \cdot R)^{-1} \cdot J^T \cdot \delta u.$$

Letting $D = (J^T \cdot J + \alpha R^T \cdot R)^{-1} \cdot J^T$, then the equation may be rewritten as:

$$\delta\sigma^* = D \cdot \delta u,$$

where $\delta\sigma^*$ as mentioned above is the calculated three-dimensional ventilation image.

Figure 6:
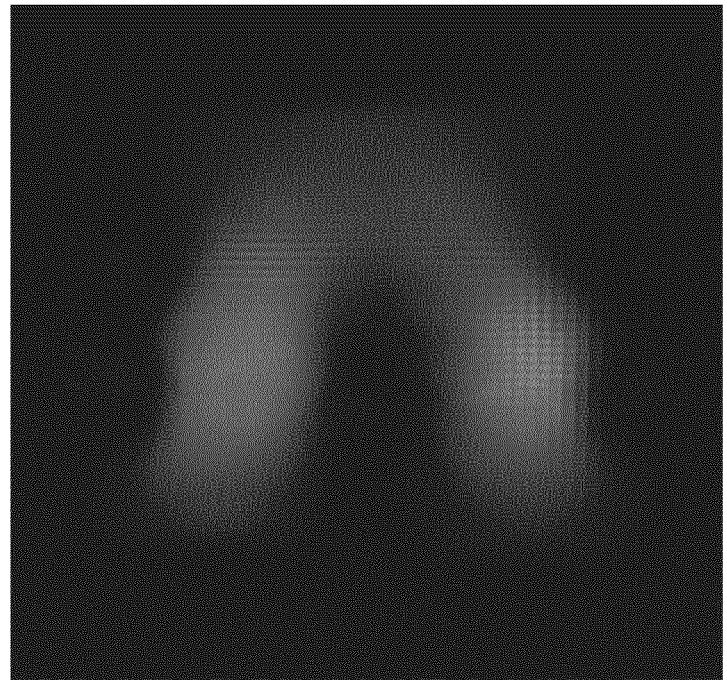
FIG. 6 is a schematic diagram of a three-dimensional ventilation image of a human body thoracic cavity generated using the three-dimensional ventilation image generation method illustrated in FIG. 3(a) according to the second embodiment of the present disclosure.

FIG. 6 is a schematic diagram of a three-dimensional ventilation image of a human body thoracic cavity generated by the method above.

In another embodiment of this step, the image reconstruction algorithm refers to a machine-learning-based method. The EIT differential imaging may be expressed as:

$$\sigma = \mathcal{F}(\delta u),$$

where $\mathcal{F}(\bullet)$ refers to a reconstruction operator, $\delta u$ denotes change of the measurement data at different moments, and $\delta\sigma$ denotes change of electrical conductivity at a corresponding moment. The machine-learning-based method comprises two phases: training and predicting. First, in the training phase, given the training data $\{\delta u^i, \delta\sigma^i\}$, a machine learning model may be trained to approximate the operator $\mathcal{F}(\bullet)$. In the predicting phase, given the differential measurement signal $\delta u$, a corresponding conductivity change may be predicted via $\mathcal{N}$:

$$\delta\sigma^* = \mathcal{N}(\delta u).$$

In addition to the image reconstruction algorithm in the above embodiments, various linear or nonlinear, iterative or non iterative, random or deterministic image reconstruction algorithms can also be used in this step.

Figure 3B:
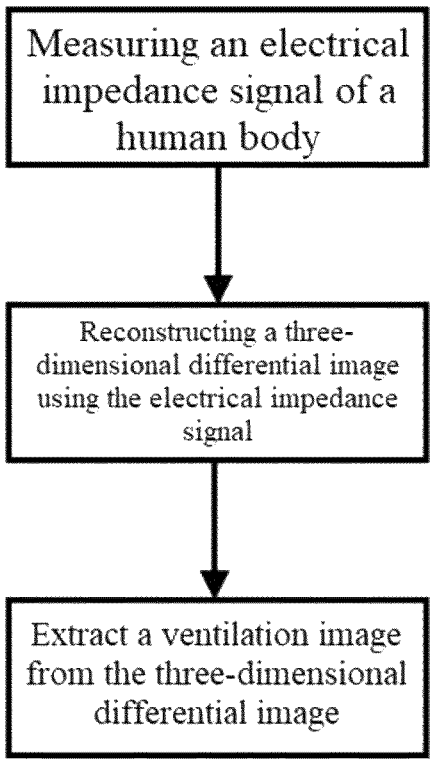
FIG. 3(b) is another flow diagram of the three-dimensional ventilation image generation method according to the second embodiment of the disclosure.

As illustrated in FIG. 3(b), the three-dimensional ventilation image generation method according to this embodiment comprises the following steps: first, electrical impedance measurement is performed on a human body thoracic region to be measured, then a three-dimensional differential image is reconstructed, and finally, a three-dimensional ventilation image is extracted from the three-dimensional differential image. Specific steps of the method are described below:

In the first step, electrical impedance measurement is performed on a human body thoracic region to be measured.

Figure 7:
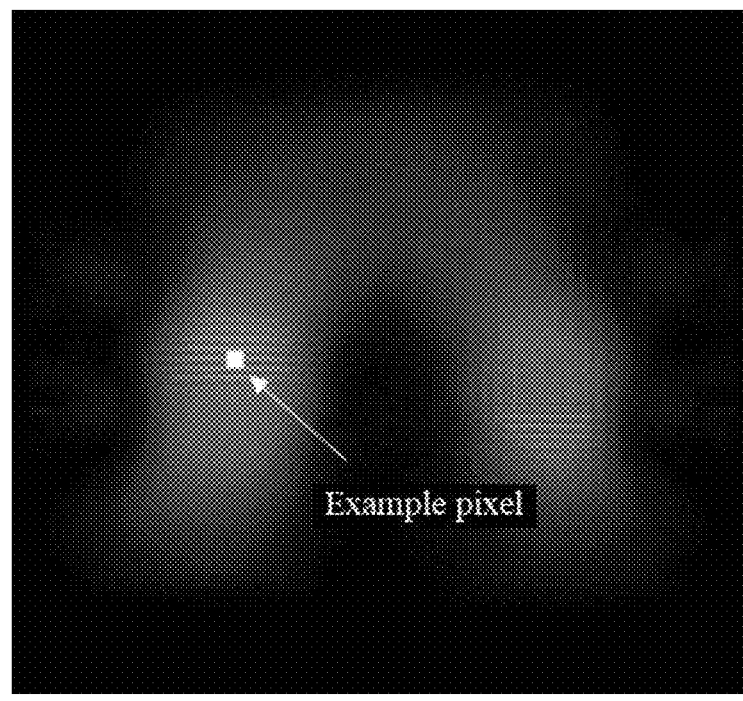
FIG. 7 is a schematic diagram of a three-dimensional differential image of a human body thoracic cavity generated using the three-dimensional ventilation image generation method illustrated in FIG. 3(b) according to the second embodiment of the present disclosure.

In the second step, a three-dimensional differential image is reconstructed by means of an image reconstruction algorithm and according to the electrical impedance signal obtained by the measurement in the preceding step. The three-dimensional differential image reflects electrical impedance change in the human body thoracic cavity to be measured, which may be induced by human body ventilation or blood perfusion. The image reconstruction algorithm may refer to an image reconstruction algorithm described above. FIG. 7 illustrates a three-dimensional differential image generated using the data illustrated in FIG. 4 and a linear differential reconstruction algorithm.

In the third step, the ventilation image is extracted from the three-dimensional differential image resulting from the preceding step. In an embodiment of this step, a ventilation image is extracted from the three-dimensional differential image using a filter. Supposing the three-dimensional differential images at N moments may be arrayed into a matrix $A=\{a_1, a_2, \ldots, a_M\}^T$, where $a_i$ (i=1, 2, ..., M) denotes a column vector composed of the values of pixel i at N moments, and M denotes the total number of the pixels in the three-dimensional image. By performing a lowpass filtering on the time sequence $a_i$ (i=1, 2, ..., M) of each pixel i, the time sequence of a corresponding pixel on the ventilation image may be obtained. Specifically, given the filter function $f(\cdot)$, then the ventilation image is $A_V=\{f(a_1), f(a_2), \ldots, f(a_M)\}^T$.

Figure 8A:
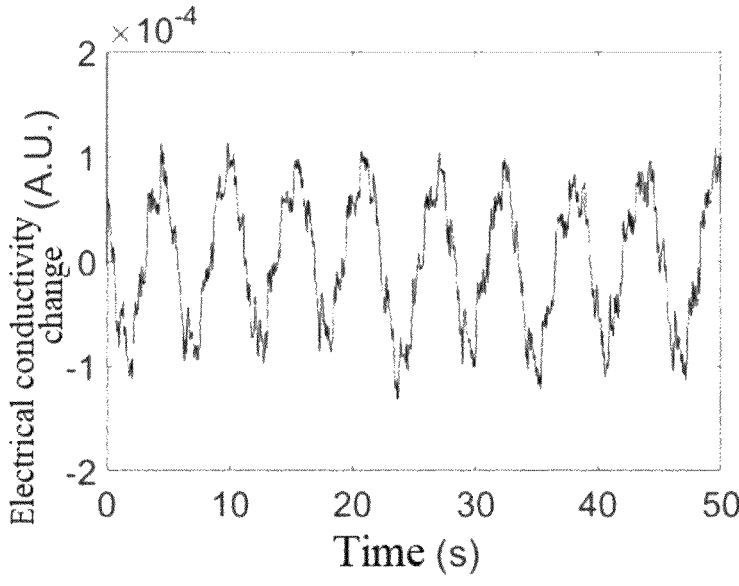
FIG. 8(a) is a temporal-domain signal schematic diagram of an example pixel in FIG. 7.
Figure 8B:
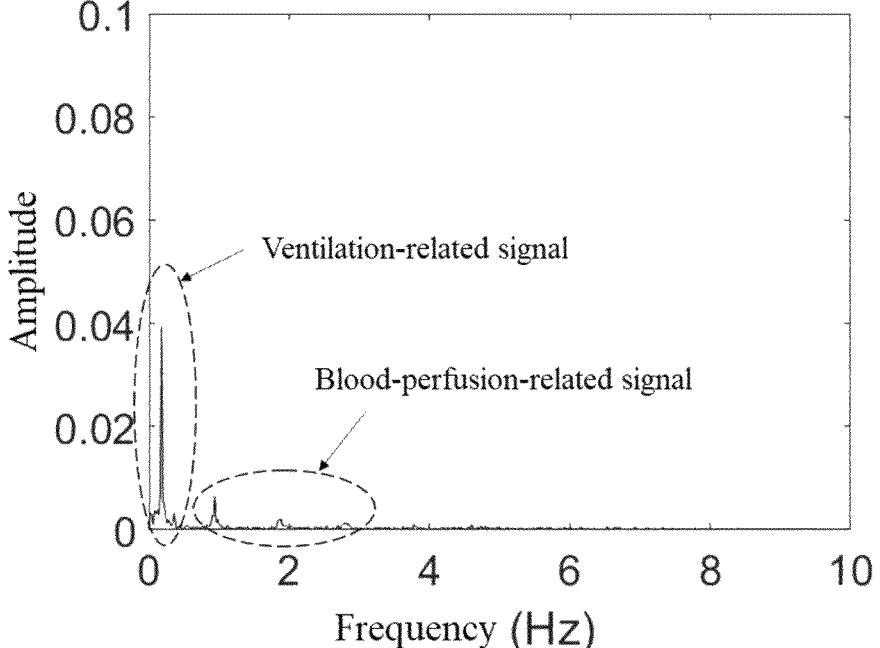
FIG. 8(b) is a frequency-domain signal schematic diagram of an example pixel in FIG. 7.

FIG. 8(a) and its corresponding spectrogram in FIG. 8(b) illustrate the time sequences of the example pixels of the three-dimensional differential image of the human body thoracic cavity in FIG. 7. FIG. 8(b) enables differentiation between the ventilation-related signal and the blood perfusion-related signal. In order to extract the ventilation-related signal, a lowpass filter is designed, which may be a finite pulse response lowpass digital filter with a cutoff frequency greater than the second harmonic frequency of the ventilation-related signal and lower than the fundamental frequency of the blood-perfusion-related signal.

Figure 9A:
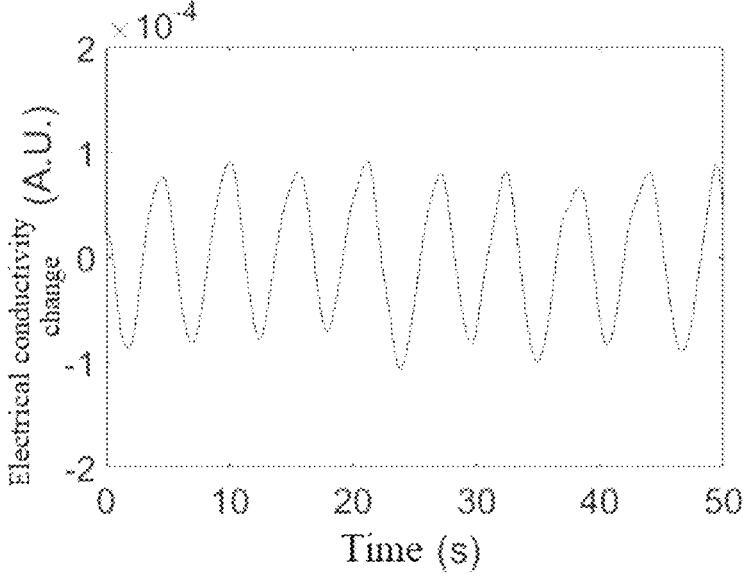
FIG. 9(*a*) is a temporal-domain signal schematic diagram of a ventilation-related signal after the example pixel in FIG. 7 has been subjected to data filtering.
Figure 9B:
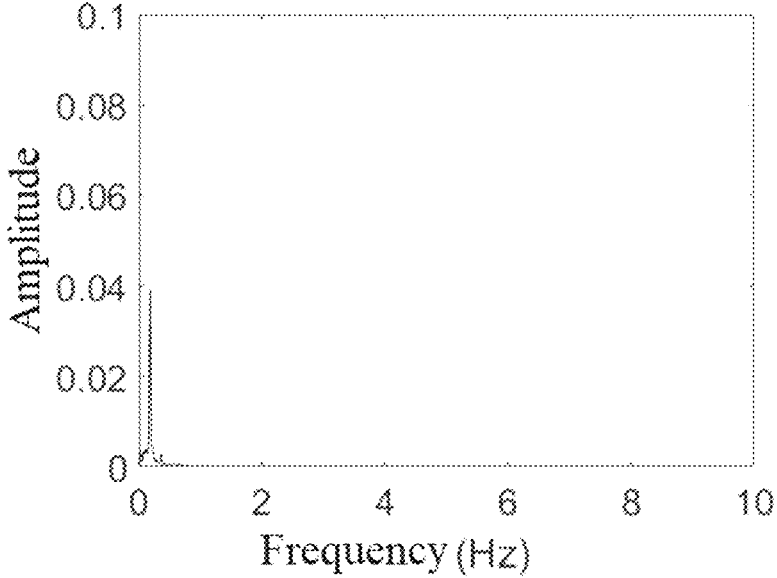
Figure 10:
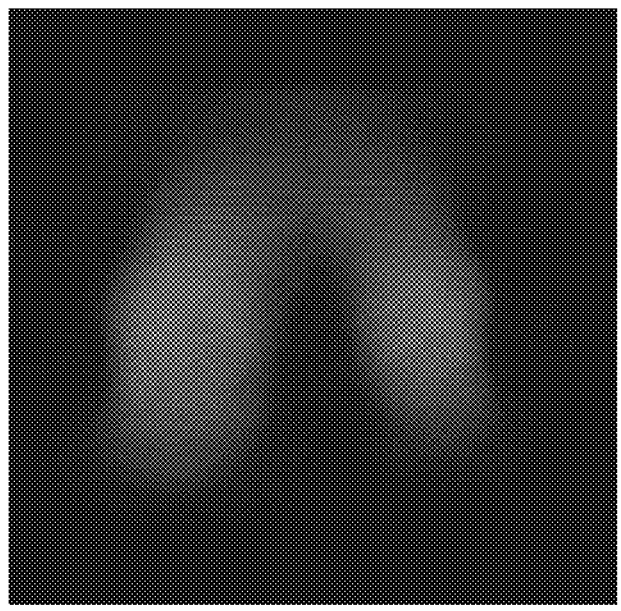
FIG. 10 is a schematic diagram of a three-dimensional ventilation image of a human body thoracic cavity generated using the three-dimensional ventilation image generation method illustrated in FIG. 3(*b*) according to the second embodiment of the present disclosure.

FIG. 9(a) and the spectrogram in FIG. 9(b) illustrate a temporal-domain signal after the example pixel in FIG. 7 has been filtered. After each pixel in the three-dimensional differential image has been subjected to the lowpass filter, a three-dimensional ventilation image may be derived, as illustrated in FIG. 10. In two further embodiments of this step, the ventilation image may be extracted using the principal component analysis algorithm and a neural-network-based algorithm, respectively.

It is noted that A.U. in FIG. 8(a), FIG. 8(b), FIG. 9(a) and FIG. 9(b) refers to arbitrary unit.

The three-dimensional ventilation image generation method applied to a human body thoracic cavity in this embodiment provides a three-dimensional ventilation image, which reflects electrical impedance change induced by human body ventilation in the human body thoracic cavity, thereby reflecting the ventilation status of the human body thoracic cavity within various volumes in the three-dimensional space.

Embodiment 3

To solve the technical problems in the existing technologies, embodiments of the present disclosure provide a three-dimensional ventilation image generation controller.

The three-dimensional ventilation image generation controller according to this embodiment comprises a memory and a processor, wherein a computer program is stored on the memory, and when being executed by the processor, implements the steps of the method recited in the first embodiment and the second embodiment, respectively.

Embodiment 4

To solve the technical problems in the existing technologies, embodiments of the present disclosure further provide a three-dimensional ventilation image generation apparatus.

The three-dimensional ventilation generation apparatus according to this embodiment comprises: an electrode array three-dimensionally distributed on the periphery of a target region to be measured, which is configured to perform electrical impedance measurement on the target region to be measured and transmit the measured electrical impedance to a three-dimensional ventilation image generation controller; and the three-dimensional ventilation image generation controller according to Embodiment 3.

The three-dimensional ventilation image generation apparatus according to this embodiment further comprises: an image displaying device configured to display the three-dimensional ventilation image generated by the three-dimensional ventilation image generation controller.

Compared with the existing technologies, one or more embodiments of the above solution may have the following advantages or beneficial effects: the three-dimensional ventilation image generation method according to the present disclosure generates a three-dimensional ventilation image using a signal extraction algorithm and an image reconstruction algorithm based on an electrical impedance signal obtained by performing electrical impedance measurement on the target region to be measured, wherein the performing electrical impedance measurement on the target region to be measured is implemented via an electrode array that is three-dimensionally distributed on the periphery of the target region to be measured, which can provide a three-dimensional ventilation image, thereby ventilation status of the human body thoracic cavity within various volumes in the three-dimensional space is reflected.

Although the embodiments of the disclosure have been disclosed above, the contents are only embodiments for facilitating the understanding of the disclosure, and are not intended for limiting the disclosure. Any person skilled in the art to which this disclosure belongs may make any modifications and variations to the form and details of the embodiments without departing from the spirits and scope of the disclosure, while the protection scope of the disclosure is governed by the scope limited in the appended claims.

The invention claimed is:

1. A three-dimensional ventilation image generation method, comprising:

reconstructing a three-dimensional image by an image reconstruction algorithm and according to an electrical impedance signal obtained by performing electrical impedance measurement on a target region to be measured, wherein the performing electrical impedance measurement on a target region to be measured is implemented by using an electrode array that is three-dimensionally distributed on the periphery of said target region to be measured, wherein the electrical impedance signal comprises a ventilation-related signal and a blood-perfusion-related signal;

listing a time sequence of each pixel in the three-dimensional image according to three-dimensional image data at a plurality of moments, wherein the time sequence of each pixel is comprised of values of each pixel at different moments;

extracting a time sequence of a ventilation-related pixel from among the time sequences of each pixel in the three-dimensional image by filtering to separate the ventilation-related signal from the blood-perfusion-related signal; and constructing a three-dimensional ventilation image according to the time sequence of the ventilation-related pixel, wherein the three-dimensional ventilation image is constructed as:

$$A_V=\{f(a_1), f(a_2), \ldots, f(a_M)\}^T$$

where $a_i$(i=1,2 ...,M) denotes a column vector composed of the values of pixel i at the plurality of moments, M denotes a total number of the pixels in the three-dimensional image, $A_v$ refers to the ventilation image, and f(•) refers to a filter function.

2. The method according to claim 1, the extracting the time sequence of the ventilation-related pixel from among the time sequences of each pixel in the three-dimensional image comprises:

extracting the time sequence of the ventilation-related pixel using a lowpass filter from among the time sequences of each pixel in the three-dimensional image, wherein the lowpass filter has a cutoff frequency greater than a second harmonic frequency of the ventilation-related signal but lower than a fundamental frequency of the blood-perfusion-related signal.

3. The method according to claim 1, wherein the extracting a time sequence of a ventilation-related pixel from among the time sequences of each pixel in the three-dimensional image is implemented by any one of a frequency-domain filtering algorithm, a principal component analysis algorithm, and a neural network algorithm.

4. The method according to claim 1, wherein the image reconstruction algorithm refers to a linear differential reconstruction algorithm or a neural-network-based image reconstruction algorithm.

5. A three-dimensional ventilation image generation controller, comprising a memory and a processor, wherein a computer program is store on the memory and, when being executed by the processor, implements steps of the three-dimensional ventilation image generation method according to claim 1.

6. A three-dimensional ventilation image generation apparatus, comprising:

an electrode array three-dimensionally distributed on an periphery of a target region to be measured, which is configured to perform electrical impedance measurement on the target region to be measured and transmit a measured electrical impedance to a three-dimensional ventilation image generation controller; and the three-dimensional ventilation image generation controller according to claim 5.

7. The method according to claim 1, wherein the extracting the time sequence of the ventilation-related pixel comprises extracting the ventilation-related signal using a lowpass filter having a cutoff frequency greater than a second harmonic frequency of the ventilation-related signal but lower than a fundamental frequency of the blood-perfusion-related signal.

8. The method according to claim 1, wherein the target region to be measured is a human body thoracic cavity, and wherein the three-dimensional ventilation image reflects an electrical impedance change induced by respiration in the human body thoracic cavity.

9. The method according to claim 1, wherein the image reconstruction algorithm comprises a linear differential reconstruction algorithm that solves a least square problem of a form: min over $\delta\sigma$ of $\|J\cdot\delta\sigma-\delta u\|^2+\alpha\|R\cdot\delta\sigma\|^2$, where J denotes a Jacobian Matrix, $\delta u$ denotes change of the electrical impedance signal at a moment t relative to a reference moment, $\delta\sigma$ denotes conductivity change induced by ventilation between the two moments, R denotes a regularization matrix, and a denotes a regularization parameter.

10. The method according to claim 1, wherein the electrode array comprises a plurality of electrodes distributed in a three-dimensional space surrounding the target region to be measured, and wherein the performing electrical impedance measurement comprises applying electrical current excitation to the electrodes alternately, and measuring voltage signals produced on other electrodes.

11. The method according to claim 1, wherein the extracting a time sequence of a ventilation-related pixel comprises:

performing a principal component analysis on the time sequences to obtain principal components $\{p_1, p_2, \ldots, p_{Nc}\}$;

using a first plurality of the principal components as a template; and performing template match filtering on the time sequences using the template to obtain the time sequence of the ventilation-related pixel.

* * * * *